United States Patent
Liu et al.

(10) Patent No.: US 7,709,238 B2
(45) Date of Patent: May 4, 2010

(54) METHOD FOR REMOVING ENZYME AND METHOD OF BASE EXCHANGE OR HYDROLYSIS OF PHOSPHOLIPID USING THE SAME

(75) Inventors: Xiaoli Liu, Osaka (JP); Naruyuki Taniwaki, Osaka (JP)

(73) Assignee: Nagase ChemteX Corporation, Osaka (JP)

( * ) Notice: Subject to any disclaimer, the term of this patent is extended or adjusted under 35 U.S.C. 154(b) by 506 days.

(21) Appl. No.: 10/592,858

(22) PCT Filed: Mar. 18, 2005

(86) PCT No.: PCT/JP2005/005631

§ 371 (c)(1),
(2), (4) Date: Sep. 14, 2006

(87) PCT Pub. No.: WO2005/090587

PCT Pub. Date: Sep. 29, 2005

(65) Prior Publication Data

US 2008/0248543 A1      Oct. 9, 2008

(30) Foreign Application Priority Data

Mar. 18, 2004   (JP) ............................. 2004-078714

(51) Int. Cl.
*C12N 9/99* (2006.01)
*C12N 9/00* (2006.01)
*C12N 9/20* (2006.01)
*C12N 9/48* (2006.01)
*C12N 9/50* (2006.01)

(52) U.S. Cl. ................ 435/184; 435/183; 435/197; 435/212; 435/219

(58) Field of Classification Search ................ None
See application file for complete search history.

(56) References Cited

U.S. PATENT DOCUMENTS

| 5,152,928 A | 10/1992 | Kudo et al. |
| 5,965,413 A * | 10/1999 | Sakai et al. ............. 435/106 |
| 6,645,742 B2 | 11/2003 | De Ferra et al. |
| 6,878,532 B1 * | 4/2005 | Meyer ................. 435/106 |
| 7,049,107 B1 * | 5/2006 | Meyer ................. 435/106 |
| 2002/0103393 A1 | 8/2002 | De Ferra et al. |

FOREIGN PATENT DOCUMENTS

| JP | 62262998 A | | 11/1987 |
| JP | 63233750 A | | 9/1988 |
| JP | 2273536 A | | 11/1990 |
| JP | 07222592 A | | 8/1995 |
| JP | 2001186898 A | | 7/2001 |
| JP | 2002193982 A | | 7/2002 |
| JP | 2002241385 A | * | 8/2002 |
| JP | 2003093086 A | | 4/2003 |
| JP | 2003319793 A | | 11/2003 |
| JP | 2004024133 A | | 1/2004 |

OTHER PUBLICATIONS

Ogino, Chiaki et al., "Purification, Characterization, and Sequence Determination of Phospholipase D Secreted by *Streptoverticillium cinnamoneum*", J. Biochem., 1999, vol. 125, No. 2, The Japanese Biochemical Society, Japan.

* cited by examiner

*Primary Examiner*—Christopher R Tate
*Assistant Examiner*—Aaron J Kosar
(74) *Attorney, Agent, or Firm*—The Webb Law Firm

(57) ABSTRACT

A method of removing an enzyme from a liquid enzyme reaction mixture used in a hydrolysis reaction or a base exchange reaction of a phospholipid is provided. The method includes the step of treating the liquid enzyme reaction mixture with a solvent mixture of water and an organic solvent, wherein the solvent mixture includes an inorganic metal salt, to remove the enzyme. Enzymes included in the reaction product can be easily removed without a treatment such as heating, and thus it becomes possible to easily produce various phospholipids that have a reduced risk of inducing an allergy, that retain a high quality and that have excellent storage stability.

5 Claims, No Drawings

METHOD FOR REMOVING ENZYME AND METHOD OF BASE EXCHANGE OR HYDROLYSIS OF PHOSPHOLIPID USING THE SAME

TECHNICAL FIELD

The present invention relates to a method for separating and removing an enzyme from a liquid reaction mixture, wherein the enzyme is used to modify phospholipids or to manufacture synthetic phospholipids, and also relates to a phospholipid base transfer method (that is, a base exchange method) and a phospholipid hydrolysis method, both of which use the method for separating and removing an enzyme.

BACKGROUND ART

The reactions for hydrolysis or base exchange of phospholipid are generally carried out in a suitable solvent in the presence of enzyme. These reactions are usually stopped by deactivating the enzyme with a treatment such as heating. For example, Japanese Laid-Open Patent Publication No. 2-273536 discloses a method for manufacturing lysophospholipids by partially hydrolyzing derivatives of phosphatidic acid with a treatment by lipase or phospholipase $A_2$ (hereinafter referred to as "$PLA_2$"). In this method, the reaction mixture is heated at an appropriate point to deactivate the enzyme and halt the reaction. Japanese Laid-Open Patent Publication No. 2001-186898 discloses a method for manufacturing a phosphatidylserine by achieving a phosphatidyl group exchange reaction between an acylglycerophospholipid and serine by using phospholipase D (hereinafter referred to as PLD). In this method, the enzyme is deactivated with a treatment such as heating or alcohol denaturation after the reaction. Japanese Laid-Open Patent Publication No. 2003-319793 discloses an acylglycerophospholipid phosphatidyl group exchange reaction by using PLD. The exchange reaction is followed by deactivating the PLD with a treatment such as heating.

As described in Japanese Laid-Open Patent Publication No. 63-233750, however, phospholipases have strong thermal resistance and thus are not sufficiently deactivated even after heating, for example, at 95° C. for about 30 minutes. The inadequate deactivation of phospholipases may cause quality problems, such as odors occurred in the hydrolysis of fats in the phospholipids. This document further teaches that deactivating the phospholipases by heating at a temperature of 100° C. or more, such as 120° C., is problematic in that phospholipids or free fatty acids resulting from treating the phospholipids with phospholipases are prone to deteriorate. Japanese Laid-Open Patent Publication No. 63-233750 discloses processing a starting material that contains phospholipid with a phospholipase, then treating the phospholipase with a protease, and then deactivating the protease by heating, to solve the problem as mentioned above.

Japanese Laid-Open Patent Publication No. 2003-93086 suggests that proteins, peptides, and enzyme can be a cause of allergy. The document also teaches that the method of Japanese Laid-Open Patent Publication No. 63-233750 is clearly problematic in terms of safety in that peptides, which are breakdown products, and proteases still remain, and they have a risk of inducing an allergy. Japanese Laid-Open Patent Publication No. 2003-93086 discloses treating a starting material that contains phospholipid with a phospholipase and then a protease, and then removing any proteins, peptides, and enzymes, to solve the problem as mentioned above. As the procedure of removing proteins or the like, filtration using a filter aid, processing using an adsorbent, and so like are exemplified. It is mentioned that the used adsorbent can be removed by filtration using the filter aid. Although this method is capable of removing proteins and the like, it requires processing such as filtration and adsorption after the reaction, and thus has the problem in that the process becomes more complicated.

Japanese Laid-Open Patent Publication No. 2002-193982 discloses adding a polar organic solvent to an liquid enzyme reaction mixture and then removing hydrophilic impurities, proteins, and inorganic salts from a solution of phosphatidylserine in the organic solvent by water extraction. The document teaches that this can reduce the activity of PLD in the solution of phosphatidylserine to below the detectable limit (0.1 IU/g), however, there is no mention regarding the protein level in the solution.

SUMMARY OF THE INVENTION

The present inventors actually performed the methods discussed above in the hydrolysis reaction or base exchange reaction of phospholipid by using an enzyme, in order to assess for deactivation of the enzyme. However, it was found that any of the methods were not able to obtain a satisfactory effect although leading to a decrease in enzyme activity (see Comparative Examples 1 to 7 below).

The inventors therefore performed keen investigations in search of a method which can more efficiently eliminate the residual enzyme activity from the liquid enzyme reaction mixture. As a result, the inventors found that washing a liquid in which an enzyme was reacted (hereafter, this is referred to as a "liquid enzyme reaction mixture") with a solvent mixture of water and organic solvent wherein the solvent mixture contains an inorganic metal salt, allowed to efficiently eliminate the residual enzyme activity and further reduce the level of protein in the liquid enzyme reaction mixture. Thereby, the inventors arrived at the present invention.

The present invention provides a method of removing an enzyme from a liquid enzyme reaction mixture used in a hydrolysis reaction or a base exchange reaction of a phospholipid, comprising: treating the liquid enzyme reaction mixture with a solvent mixture of water and an organic solvent, wherein the solvent mixture contains an inorganic metal salt, to remove the enzyme.

The present invention also provides a method for phospholipid base exchange, comprising: obtaining a liquid enzyme reaction mixture by reacting a phospholipid with a compound having an alcoholic hydroxyl group in the presence of an enzyme, wherein the compound having an alcoholic hydroxyl group is selected from the group consisting of alcohol, saccharide, and a cyclic compound having a hydroxyl group and wherein the enzyme is capable of transferring a base in the phospholipid to the compound; and removing the enzyme by treating the liquid enzyme reaction mixture with a solvent mixture of water and an organic solvent, wherein the solvent mixture contains an inorganic metal salt.

Further, the present invention provides a method for phospholipid hydrolysis, comprising: obtaining a liquid enzyme reaction mixture by reacting a phospholipid with an enzyme in the presence of water, wherein the enzyme is capable of hydrolyzing the phospholipid; and removing the enzyme by treating the liquid enzyme reaction mixture with a solvent mixture of water and an organic solvent, wherein the solvent mixture contains an inorganic metal salt.

In an embodiment, the inorganic metal salt is at least one metal salt selected from the group consisting of sodium chloride, sodium sulfate, potassium chloride, calcium chloride, and magnesium sulfate.

In other embodiment, the organic solvent is a polar solvent.

In a further embodiment, the polar organic solvent is at least one solvent selected from the group consisting of acetone, ethanol, methanol, isopropanol, and glycerol.

Further, in a different embodiment, the solvent mixture includes water at 30 to 70 percent by volume and the organic solvent at 70 to 30 percent by volume, and contains the inorganic metal salt at 5 to 25 percent weight by volume.

DETAILED DESCRIPTION OF THE INVENTION

First, methods for base exchange and for hydrolysis of phospholipid by using an enzyme, and then, a method of removing an enzyme from those liquid enzyme reaction mixtures are described below.

A. Method for Phospholipid Base Exchange by Using Enzyme

The phospholipid base exchange method of the present invention includes steps of obtaining an liquid enzyme reaction mixture by reacting a phospholipid with an acceptor alcohol, wherein the acceptor alcohol is selected from the group consisting of alcohol, saccharide, and a cyclic compound with a hydroxyl group, in the presence of an enzyme, wherein the enzyme is capable of transferring the base of the phospholipid to the alcohol compound; and removing the enzyme by treating the liquid enzyme reaction mixture with a solvent mixture of water and an organic solvent, wherein the solvent mixture contains an inorganic metal salt. Here, first, the procedure of obtaining the liquid enzyme reaction mixture by a base exchange reaction is described.

A-1 Starting Phospholipid Material

There are no particular limitations regarding the phospholipid that is used in the present invention (as a starting phospholipid material), and examples thereof include phosphatidylcholine (PC), phosphatidylethanolamine (PE), phosphatidylserine (PS), phosphatidic acid (PA), and phosphatidylglycerol (PG).

The starting phospholipid material includes, in addition to pure compounds as mentioned above, egg yolk phospholipid, soybean phospholipid, rapeseed phospholipid, and fish and shellfish phospholipid, which include the compounds. For example, egg yolk phospholipid includes 73.0% PC, 15.0% PE, and 0.6% PI, and soybean phospholipid includes 38.2% PC, 17.3% PE, and 16.0% PI (for both, see "Shinshokuhin kinou sozai no kaihatsu", (meaning "Development of New Function Material for Food"), edited by Akira Ohta, published by CMC, 1996). Thus, naturally occurring phospholipids which include the compounds as mentioned above are useful as a starting material.

The egg yolk phospholipid, soybean phospholipid, rapeseed phospholipid, and fish and shellfish phospholipid as mentioned above, need not be highly purified. For example, a crude extract or crude purified product that also contains any components, such as proteins, fats, polysaccharides, and salts, other than the phospholipids can be adopted as a starting material as long as the components do not hinder the enzyme reaction. It is also possible to use chemically or enzymatically synthesized PC or PE as a starting phospholipid material.

A-2 Compound having an Alcoholic Hydroxyl Group

The compound having an alcoholic hydroxyl group that is used in the present invention is used as an acceptor for a base part, such as a phosphatidyl group of an acylglycerophospholipid, in the phospholipid base transfer. Examples of the compound having an alcoholic hydroxyl group include alcohol, saccharide, and a cyclic compound with a hydroxyl group.

Examples of the alcohol include monohydric alcohol, polyhydric alcohol (including dihydric alcohol and trihydric alcohol; also referred to as polyol), and nitrogen-containing alcohol. Examples of the monohydric alcohol include methanol, ethanol, and propanol, and examples of the polyhydric alcohol include glycerol, ethylene glycol, and propylene glycol. Ascorbic acid also is included. Examples of the nitrogen-containing alcohol include amino acid such as serine, and 1-amino-2-propanol.

Examples of the saccharide include monosaccharide such as glucose, oligosaccharide including disaccharide such as sucrose, and N-acetyl-D-glucosamine. The examples also include nucleotide such as adenosine, guanosine, inosine, xanthosine, deoxyadenosine, and deoxyguanosine, which have a saccharide such as ribose or deoxyribose.

Examples of the cyclic compound having a hydroxyl group include kojic acid and arbutin.

A-3 Enzyme

The enzyme that is used in the method for phospholipid base transfer according to the present invention includes PLD.

Examples of the PLD include PLD derived from plant, including PLD from cabbage or peanuts, and PLD from microorganism of the genus Streptomyces. Of these, PLD produced by *Streptomyces cinnamoneum* is preferably used. The PLD produced by this microorganism has a molecular weight of about 54,000, its optimal pH is approximately 5 to 6, and its optimal temperature is 40 to 60° C. (Chiaki Ogmo et al., J. Biol. Chem., vol. 125, pp. 263-269 (1999)).

Mutant strains in which the productivity of PLD producing strains has been increased and recombinant microorganisms obtained by introducing the PLD gene isolated from the above microorganism into a host of the same species or a different species in order to improve PLD production, and PLD enzymes derived therefrom may be used in the present invention.

A-4 Base Exchange Reaction

The base exchange reaction is achieved by reacting a starting phospholipid material with a compound having an alcoholic hydroxyl group (hereinafter, may be referred to as an "acceptor alcohol") in the presence of an enzyme having base transfer activity (PLD).

There are no particular limitations regarding the mole ratio of the starting phospholipid material and the acceptor alcohol, and the mole ratio can be suitably determined in accordance with the types of the starting phospholipid material and the acceptor alcohol. It is generally preferable that the ratio (mole ratio) of acceptor alcohol/starting phospholipid material is in the order of 0.001 to 200. For example, in the case of PE, it is generally preferable that the ratio (mole ratio) of acceptor alcohol/PE is from 0.01 to 100.

There are no particular limitations regarding the amount of the enzyme that is used in the base exchange reaction, and this can be determined in accordance with the types of the starting phospholipid material, the acceptor, and the enzyme. For example, in the case of PLD, 20 to 8000 units of PLD can be used per 1 g PE. Here, one unit of the activity of the enzyme refers to the amount of enzyme with which 1 μmol of choline is released per minute on reacting the enzyme with 95% soybean PC (Phosphatide Extract, Soybean (Granules), made by Avanti Polar Lipid Inc.) as the substrate at 37° C. in a 40 mM acetate buffer (pH 5.5, 1 mM $CaCl_2$, 0.3% Triton X-100) with a substrate concentration of 0.16%.

A water-based solvent, an organic solvent, and the solvent mixture of a water-based solvent and an organic solvent can be used as a reaction solvent for the base exchange reaction. The water-based solvent for the reaction includes water and/or an aqueous buffer. Preferable examples of water that can be used include ion-exchange water, purified water, and distilled water, but it is also possible to use tap water. An aqueous buffer such as an acetate buffer at a pH of 4 to 6, or a phosphate buffer at a pH of 7 to 8 is preferably used. Examples of the organic solvent for the reaction include aliphatic hydrocarbon such as n-heptane, n-hexane, and petroleum ether; cyclic aliphatic hydrocarbon such as cyclopentane and cyclohexane; ether such as diethyl ether and tetrahydrofuran; ester such as methyl acetate and ethyl acetate; and halogenated hydrocarbon such as carbon tetrachloride and chloroform. The organic solvent for the reaction can be a single solvent or a mixture of two or more solvents. The water-based solvent or organic solvent for the reaction can be used in combination with a solvent that enhances the base exchange reaction, such as acetone.

If a solvent mixture of a water-based solvent and an organic solvent is used for the reaction, then the blend ratio can be suitably chosen in accordance with the type of the organic solvent used. There are no particular limitations regarding the blend ratio. In general, in order to efficiently achieve a base (phosphatidyl group) exchange reaction while preventing a hydrolysis reaction as a side reaction at a base (phosphatidyl group) of phospholipid, the amount of the water-based solvent is preferably not more than 10% by volume in the reaction system.

The amount of the phospholipid used in the enzyme reaction is preferably 1 to 50% (w/v), and more preferably 5 to 30% (w/v), by volume of reaction solvent. If the amount of the phospholipid is greater than 50% (w/v), the viscosity of the solution in which the starting phospholipid material is dissolved may be high, leading to a decrease in the reaction efficiency. On the other hand, if the amount of the phospholipid is less than 1% (w/v), only a very small amount of the phospholipid can be treated at one time, leading to a decrease in the processing efficiency.

The temperature of the base exchange reaction is preferably 10 to 70° C. and more preferably 25 to 50° C. The time required for the reaction varies depending on the amount of the enzyme and the reaction temperature, but is generally between 0.5 and 48 hours. It is preferable to suitably perform a procedure of dispersing such as agitation or mixing in the method according to the present invention, in view of the dispersivity of the phospholipid and also the blendability of the solvent mixture for the reaction that is carried out in a two-phase system of an aqueous layer and an organic solvent layer.

The above reaction achieves a base exchange in the phospholipid, so as to produce a phospholipid corresponding to the type of the acceptor alcohol. For example, phosphatidylglycerol (PG) and phosphatidylserine (PS) are produced by glycerol and serine which are employed as the alcohol, respectively.

Then, the enzyme is removed from the liquid enzyme reaction mixture to purify the reaction product. The procedure of removing the enzyme is described in "D. Method of Removing Enzyme from the Liquid Enzyme Reaction Mixture."

B. Method for Phospholipid Hydrolysis by Using Enzyme

The method for phospholipid hydrolysis according to the present invention includes steps of obtaining an liquid enzyme reaction mixture by reacting a phospholipid with an enzyme, wherein the enzyme is capable of hydrolyzing the phospholipid, in the presence of water; and removing the enzyme by treating the liquid enzyme reaction mixture with a solvent mixture of water and an organic solvent, wherein the solvent mixture contains an inorganic metal salt. Here, first, the procedure of obtaining the liquid enzyme reaction mixture by hydrolysis reaction is described.

B-1. Starting Phospholipid Material

The phospholipid as described in A-1 above can be used as a starting phospholipid material used for hydrolysis.

B-2. Enzyme

There are no particular limitations regarding the enzyme that is used for hydrolysis of the phospholipid, as long as it is capable of hydrolyzing a fatty acid part and/or a base part of the phospholipid. Examples of the enzyme include lipase, phospholipase A1 (hereinafter "$PLA_1$"), $PLA_2$, phospholipase B (hereinafter "PLB"), phospholipase C (hereinafter "PLC"), PLD, and sphingomyelinase.

For PLD, the PLD as discussed in A-3 above may be used. Examples of $PLA_2$ include $PLA_2$ derived from animal (for example, $PLA_2$ from pig pancreas) and $PLA_2$ derived from microorganism (such as $PLA_2$ from microorganism of the genus *Streptomyces*).

Examples of $PLA_1$, PLB, PLC, and lipase include lipases derived from microorganism, including phospholipase and lipase from microorganism of the genus *Aspergillus* or *Streptomyces*.

Mutant strains in which the productivity of the enzyme-producing strains has been increased and recombinant microorganisms obtained by introducing the enzyme gene isolated from the above microorganism into a host of the same species or a different species in order to improve the enzyme production, and enzymes derived therefrom may be used in the present invention.

B-3. Hydrolysis Reaction

The hydrolysis reaction is achieved by reacting the starting phospholipid material with the hydrolytic enzyme in the presence of water. There are no particular limitations regarding the mole ratio of the phospholipid and the water in the phospholipid hydrolysis reaction. The use of 0.01 to 100 moles of water per 1 mole of phospholipid is appropriate.

There are no particular limitations regarding the amount of the enzyme used in the hydrolysis reaction, and this can be suitably determined in accordance with the types of the starting phospholipid material and the enzyme. For example, in the case of PLD, 20 to 8000 units of PLD can be used per 1 g PE as in A-4 discussed above.

$PLA_2$ can be used, for example, in the range of 20 to 8000 units per 1 g PE. One unit of $PLA_2$ refers to the amount of enzyme with which 1 μmol of fatty acid is released per minute on reacting the enzyme with soybean paste lecithin (P-3644 Sigma PC content 40%) as the substrate at 37° C. in a 25 mM Tris-HCl buffer (pH 8.0, 2.5 mM $CaCl_2$, 0.002% Triton X-100) with a substrate concentration of 1.25%.

Lipase can be used in the range of 20 to 50,000 units per 1 g PE. One unit of lipase refers to the amount of enzyme with which acid corresponding to 1 μmol oleic acid is released when the emulsified mixture of olive oil, 2% PVA, and McIlvaine buffer (pH 7.0) at a volume ratio 2:3:1 is taken as the substrate, and 1 ml of diluted lipase solution is mixed per 4 ml of the substrate and reacted at 37° C. for 60 minutes.

As the reaction solvent to be used in the hydrolysis reaction, a water-based solvent or a solvent mixture of a water-based solvent and an organic solvent as discussed in A-4 Base Exchange Reaction can be used. In view of the solubility of the phospholipid in water, it is preferable to use a solvent mixture of a water-based solvent and an organic solvent. For example, a water-based solvent such as Tris-HCl buffer at a pH of 7 to 9 also may be preferably used.

If a solvent mixture of a water-based solvent and an organic solvent is used, then the blend ratio can be suitably chosen in accordance with the type of the organic solvent used. There are no particular limitations regarding the blend ratio of the water-based solvent and the organic solvent. In terms of enhancing the hydrolysis reaction, it is preferable that the amount of the water-based solvent is not less than 10% by volume in the reaction system.

The amount of the phospholipid used in the enzyme reaction preferably is 1 to 50% (w/v), and more preferably 5 to 30% (w/v), by volume of reaction solvent. If the amount of the phospholipid is greater than 50% (w/v), the viscosity in the solution in which the starting phospholipid material is dissolved may be high, leading to a decrease in the reaction efficiency. On the other hand, if the amount of the phospholipid is less than 1% (w/v), only a very small amount of the phospholipid can be treated at one time, leading to a decrease in the processing efficiency.

The temperature of the hydrolysis reaction depends on the physical and chemical properties of the enzyme used. For example, in the case of $PLA_2$ derived from an animal, the temperature is preferably 10 to 70° C., and more preferably 25 to 50° C. The time required by the reaction varies depending on the target reaction, the amount of the enzyme and the reaction temperature, but is generally between 0.5 and 48 hours. It is preferable to suitably perform a procedure of dispersing such as agitation or mixing in the method according to the present invention, in view of the dispersivity of the phospholipid and also the blendability of the solvent mixture for the reaction that is carried out in a two phase system of an aqueous layer and an organic solvent layer.

The above reaction achieves hydrolysis of the phospholipid. Thereby, lysophosphatidylcholine (LPC) is produced from phosphatidylcholine (PC), lysophosphatidylethanolamine (LPE) is produced from phosphatidylethanolamine (PE), or phosphatidic acid (PA) is produced from PC or PE.

Then, the enzyme is removed from the liquid enzyme reaction mixture to purify the reaction product. The procedure of removing the enzyme is described in "D. Method of Removing Enzyme from the Liquid Enzyme Reaction Mixture."

C. Processing the Liquid Enzyme Reaction Mixture Prior to Enzyme Removal

The liquid enzyme reaction mixture obtained in the base exchange method of A. or in the hydrolysis method of B. is either a system (1) that includes an organic solvent or (2) that is water-based. For each of these systems, the processing of the liquid enzyme reaction mixture before enzyme removal is discussed below.

(1) System Including an Organic Solvent

In the case that the liquid enzyme reaction mixture is a system including an organic solvent solely, the enzyme can be removed subsequently.

In the case that the liquid enzyme reaction mixture is a solvent mixture system of an organic solvent and a water-based solvent, if the organic solvent and the water-based solvent can be separated, then it is preferable to remove the water-based solvent in advance. If the organic solvent and the water-based solvent cannot be separated well, or if the organic solvent and the water-based solvent are emulsified, then the enzyme removal can be performed subsequently without removing the water-based solvent.

(2) Water-Based System

In the case that the liquid enzyme reaction mixture is water-based, it is preferable to add an organic solvent for extraction, perform solvent fractioning, and then remove the fractioned water-based solvent. The organic solvents as listed as the organic solvent for the reaction in A-4 above can be used as the organic solvent for extraction. However, in this case as well, the enzyme removal can be performed subsequently without removing the water-based solvent if the organic solvent for extraction and the water-based solvent cannot be separated well, or if the organic solvent for extraction and the water-based solvent are emulsified.

D. Method of Removing Enzyme from the Liquid Enzyme Reaction Mixture

The method of removing the enzyme from the liquid enzyme reaction mixture obtained in C. includes a step of treating the liquid enzyme reaction mixture with a solvent mixture of water and organic solvent, wherein the solvent mixture contains an inorganic metal salt (hereinafter, referred to simply as a "solvent mixture for washing"), in order to remove the enzyme.

The liquid enzyme reaction mixture obtained in C. includes an enzyme, a starting phospholipid material, a reaction product, and a water-based solvent and/or an organic solvent. The feature of the present invention is that the enzyme is removed by treating the liquid enzyme reaction mixture with a solvent mixture of water and organic solvent, wherein the solvent mixture contains an inorganic metal salt.

D-1. Inorganic Metal Salt

Examples of the inorganic metal salt used in the present invention include inorganic salts of monovalent metal, divalent metal, or polyvalent metal.

Preferable examples of the inorganic salt of monovalent metal that can be used include inorganic salts of alkali metal and inorganic ammonium salts. Preferable examples of the alkali metal that can be used include sodium (Na), potassium (K), and lithium (Li), and sodium is most preferable. Preferable examples of an inorganic compound that forms a salt with the alkali metal or ammonia that can be used include hydrochloric acid, sulfuric acid, and carbonic acid. Preferable examples of the monovalent inorganic metal salts that can be used include sodium chloride (NaCl), sodium sulfate ($Na_2SO_4$), potassium chloride (KCl), and potassium sulfate ($K_2SO_4$).

For the inorganic salts of divalent or polyvalent metal, divalent or polyvalent metals such as alkaline earth metal can be used. Preferably magnesium (Mg) or calcium (Ca) is used, and examples of inorganic salts of these include magnesium chloride ($MgCl_2$), magnesium sulfate ($MgSO_4$), calcium chloride ($CaCl_2$), and calcium sulfate ($CaSO_4$).

The inorganic metal salt can be a single inorganic metal salt or a combination of two or more inorganic metal salts.

D-2. Organic Solvent for Washing

There are no particular limitations regarding the organic solvent used for enzyme removal (organic solvent for washing), as long as it is polar. An organic solvent such as alcohol (in particular, lower alcohol) and acetone is preferably used. Examples of the lower alcohol include alcohols with one to seven carbon atoms. Specifically, methanol, ethanol, isopropanol, and glycerol are preferably used.

The organic solvent can be a single organic solvent or a combination of two or more organic solvents.

D-3. Solvent mixture of Water and an Organic Solvent wherein the Solvent Mixture Contains an Inorganic Metal Salt (Solvent mixture for washing)

In general, the water and the organic solvent are mixed to a ratio of 1:9 to 9:1, preferably 3:7 to 7:3, and more preferably 4:6 to 6:4 by volume.

The inorganic metal salt is included in the solvent mixture at 3 to 25 weight/volume % (hereinafter, w/v%), preferably 5 to 20 w/v %, and more preferably 5 to 10 w/v %.

It should be noted that there are no particular limitations regarding the manner in which the solvent mixture for washing is prepared. For example, it can be prepared by preparing a solution of the inorganic metal salt at an appropriate concentration in water and mixing it with an appropriate amount of the organic solvent. Alternatively, an appropriate amount of inorganic metal salt can be added to the solvent mixture of the water and the organic solvent. Specifically, a mixed solution of acetone and a 15 w/v % NaCl aqueous solution at 1:1 (v/v) (a 50 v/v % acetone-water solvent mixture containing 7.5 w/v % NaCl) is illustrated. Similarly, a 50 v/v % ethanol-water solvent mixture containing 7.5 w/v % NaCl, a 50 v/v % isopropanol-water solvent mixture containing 7.5 w/v % NaCl, and a 50 v/v % methanol-water solvent mixture containing 7.5 w/v % NaCl are illustrated. It should be apparent that these are only illustrative examples.

D-4. Treating the Liquid Enzyme Reaction Mixture

The treatment of the liquid enzyme reaction mixture includes washing the liquid enzyme reaction mixture obtained in C. with the solvent mixture for washing. Such washing is achieved by mixing the liquid enzyme reaction mixture with the solvent mixture for washing thoroughly, and then separating and then removing the solvent mixture for washing therefrom by centrifugation or still standing.

The solvent mixture for washing can be added at a proportion of at least 1/10 of the volume of the liquid enzyme reaction mixture obtained in C. In view of the processing efficiency, the amount of the solvent mixture for washing used is preferably 3/10 to 3/1 (v/v), and more preferably 5/10 to 1/1 (v/v), of the volume of the liquid enzyme reaction mixture.

After washing, a phospholipid-containing organic solvent phase is recovered. The treatment with the solvent mixture for washing can be repeated if necessary.

The treatment of the enzyme reaction mixture with the solvent mixture for washing can be achieved not only by preparing the solvent mixture and adding it to the enzyme reaction mixture as mentioned above, but also by adding the inorganic metal salt, water, and the organic solvent directly to the enzyme reaction mixture until the amounts to be added as defined above. There are no particular limitations regarding the order in which the components are added. Alternatively, it is possible to add an aqueous solution containing the inorganic metal salt at the given level and the organic solvent to the enzyme reaction mixture. Thus, it is only necessary that the resultant enzyme reaction mixture can include the defined amount of the solvent mixture.

The inorganic metal salt, water, or polar solvent which can constitute the solvent mixture for washing and has already been included in the liquid enzyme reaction mixture can be also utilized as the component of the solvent mixture for washing.

If the phospholipid-containing organic solvent phase obtained after washing is contaminated with an inorganic metal salt which is a component the solvent mixture for washing, then the inorganic metal salt can be easily removed by further washing with a liquid mixture of water and a polar organic solvent.

E. Recovery of the Reaction Product

The reaction product of interest can be recovered from the phospholipid-containing organic solvent phase obtained in D. by means commonly performed by those skilled in the art. For example, the reaction product can be recovered by means such as extraction with an organic solvent capable of dissolving the reaction product followed by removal of the organic solvent under reduced pressure, and then, if necessary, purified. The resultant product either includes none or little of the enzyme used in the reaction, and thus can be stored stably.

EXAMPLES

The examples are shown below to explain the invention in more specific detail, but not limit the invention thereto.

<Method of Analysis>

(Confirming the Reaction)

In the following preparation examples, the progress of the reaction was confirmed as follows. A portion of the liquid reaction mixture was taken, whole solvent was removed by evaporation under reduced pressure, the dried residue was dissolved in a 7:3 chloroform:acetonitrile mixture, and the product such as PS, PA, and LPA was detected through high performance liquid chromatography (hereinafter referred to as "HPLC") under the following conditions:

Column Used: Unisil Q NH2 (inner diameter 4.6 mm×25 cm) made by GL Sciences

Moving Phase: acetonitrile:methanol:10 mM ammonium dihydrogen phosphate=619:291:90 (v/v/v)

Flow Rate: 1.3 ml/min

Column Temperature: 37° C.

Detection: UV 205 nm (Definition and Method for Measuring of Enzyme Activity)

The activities of the enzymes in the following preparation examples and examination examples were defined as follows. As for the residual enzyme activity, a portion of the phospholipid was picked, whole solvent was removed by evaporation under reduced pressure, and then the lecithin obtained was measured with the following method. The residual enzyme activity was shown as the activity per 1 g lecithin.

Phospholipase D (PLD):

The enzyme was reacted with 95% soybean phosphatidylcholine (PC) (Phosphatide Extract, Soybean (Granules), made by Avanti Polar Lipid Inc.) as the substrate at 37° C. in a 40 mM acetate buffer (pH 5.5, 1 mM $CaCl_2$, 0.3% Triton X-100) with a substrate concentration of 0.16 wt %, and the enzyme activity was measured. As for the enzyme activity, the amount of enzyme with which 1 μmol of choline is released per minute is regarded as 1 U.

Phospholipase $A_2$ ($PLA_2$):

The enzyme was reacted with soybean paste lecithin (P-3644 Sigma PC content 40%) as the substrate at 37° C. in a 25 mM Tris-HCl buffer (pH 8.0, 2.5 mM $CaCl_2$, 0.002% Triton X-100) with a substrate concentration of 1.25 wt %. The amount of enzyme with which 1 μmol of fatty acid is released per minute is regarded as 1 U.

Lipase:

The emulsified mixture of olive oil, 2% PVA, and McIlvaine buffer (pH 7.0) at a volume ratio 2:3:1 was taken as the substrate, and 1 ml diluted lipase solution was mixed with 4 ml of the substrate and reacted at 37° C. for 60 minutes. The amount of enzyme with which releases acid corresponding to 1 μmol oleic acid is released is regarded as 1 U.

Protease:

1 ml of liquid enzyme was added to 5 ml of 0.6% milk casein (pH 7.5, 0.04 M phosphate buffer), and reacted for ten minutes at 30° C. The activity that releases Folin's color corresponding to 1 μg tyrosine per minute as the TCA soluble component is regarded as 1 U.

(Quantifying the Residual Protein)

After solvent was removed under reduced pressure, the phospholipid fraction was dissolved in chloroform and then subjected to centrifugation, and the protein was withdrawn as a chloroform impurity. The protein withdrawn was washed with chloroform several times, and then the chloroform was removed under reduced pressure to yield the protein to be quantified. The protein was quantified using the Protein Quantification Kit—Wide Range (Dojindo Molecular Technologies, Inc.), taking bovine serum albumin as a marker.

<Preparation of the Reaction Solution>

Preparation Example 1

Preparation of Liquid Enzyme Reaction Mixture in which the Base Exchange Reaction has been Achieved Lecithin (SLP-PI powder; made by Tsuji Oil Mill co., Ltd) and serine were dissolved in a two-phase solvent mixture obtained by mixing hexane, acetone, and 0.2 M acetate buffer (pH 4.0) at a ratio of 78/14/8 (by volume) so that the lecithin to serine ratio was 1:7 to 10 (by weight), and then PLD (PLD Nagase (made by Nagase ChemteX Corporation)) was added, and reacted for five hours at 30° C. while stirring, to produce phosphatidylserine (PS). The progress of the reaction was monitored with HPLC as discussed above.

When the reaction was finished, the product was allowed to sit and separate into two phases of an organic solvent phase and an aqueous phase, and then the organic solvent phase, which contains PS, was recovered. Hereinafter, the organic solvent, which contains PS, is referred to as the phospholipid fraction I.

Preparation Example 2

Preparation of Liquid Enzyme Reaction Mixture in which Hydrolysis has been Achieved—1

Lecithin (Ultralec P: made by ADM) was dispersed to 5 to 25% in 0.2 M acetate buffer (pH 5.5), and then PLD (PLD Nagase (made by Nagase ChemteX Corporation)) was added and reacted for 16 hours at 50° C. while stirring, to produce phosphatidic acid (PA). Hereinafter, the water-based solvent, which contains PA, is referred to as the phospholipid fraction II. The progress of the reaction was monitored with HPLC as discussed above.

Preparation Example 3

Preparation of Liquid Enzyme Reaction Mixture in which Hydrolysis has been Achieved—2

A portion of the phospholipid fraction II obtained in Preparation Example 2 was picked, and then a solvent mixture of heptane and acetone at a 1:2 heptane:acetone ratio (v/v) was added and agitated in a twice volume of the volume of the picked phospholipid fraction, and then the water-based solvent was removed, then the organic solvent phase containing the PA was recovered. Hereinafter, the organic solvent phase containing the PA is referred to as the phospholipid fraction III.

Preparation Example 4

Preparation of Liquid Enzyme Reaction Mixture in which Hydrolysis has been Achieved—3

To the phospholipid fraction III obtained in Preparation Example 3 was added 0.1 M Tris-HCl (pH 8.0, containing 40 mM $CaCl_2$) as a water-based solvent, then $PLA_2$ (PLA2 Nagase (made by Nagase ChemteX Corporation)) was added and reacted for 16 hours at 30° C. while stirring, to produce lysophosphatidic acid (LPA). The progress of the reaction was monitored with HPLC as discussed above. When the reaction was finished, the product was allowed to sit and separate the water-based solvent, and then the organic solvent phase, which contains LPA, was recovered. Hereinafter, the organic solvent phase, which contains LPA, is referred to as the phospholipid fraction IV.

Preparation Example 5

Preparation of Liquid Enzyme Reaction Mixture in which Hydrolysis has been Achieved—4

To the phospholipid fraction III obtained in Preparation Example 3 was added 0.1 M Tris-HCl (pH 8.0, containing 40 mM $CaCl_2$) as a water-based solvent, then lipase (Lilipase A-10 (made by Nagase ChemteX Corporation)) was added and reacted for 16 hours at 30° C. while stirring, to produce LPA. The progress of the reaction was monitored with HPLC as discussed above. When the reaction was finished, the product was allowed to sit and separate the water-based solvent, and then the organic solvent phase, which contains LPA, was recovered. Hereinafter, the organic solvent phase, which contains LPA, is referred to as the phospholipid fraction V.

Preparation Example 6

Preparation of Liquid Enzyme Reaction Mixture Treated with Protease

To the phospholipid fraction II, which contains the product PA and the enzyme PLD, Protease (trade name: Bioprase conc. (made by Nagase ChemteX Corporation)) was added at 20 U per 1g lecithin and agitated for one hour at 60° C., after which the water-based solvent, which contains PA, was recovered. Hereinafter, the water-based solvent, which contains PA, is referred to as the phospholipid fraction VI.

The residual PLD activity or the residual $PLA_2$ activity of the phospholipid fractions (I to VI) was 10 to 60 U per 1 g lecithin. The phospholipid fractions I through VI were subsequently used to conduct the following comparative examples and examination examples.

<Evaluation for Enzyme Deactivation Using Conventional Methods>

Comparative Example 1

Evaluation for PLD Removal by Heating

The phospholipid fraction I obtained in Preparation Example 1 was treated for 15 hours at the temperatures shown in Table 1, and then the residual activity of the PLD was measured. The residual activity of the PLD was measured as discussed above. The results are shown in Table 1.

TABLE 1

| Heating Temperature | Residual PLD Activity (U/g Lecithin) | Acid Value | Peroxide Value |
|---|---|---|---|
| no heating | 65.5 | 22.8 | 4.4 |
| 60° C. | 60.0 | 24.1 | 4.7 |
| 70° C. | 52.4 | 28.1 | 7.7 |
| 80° C. | 42.9 | 32.6 | 10.7 |
| 90° C. | 36.9 | 44.8 | 72.3 |

Table 1 clearly shows that the activity of PLD was reduced by heating for 15 hours, but more than half of activity still remained. From this it could be deduced that PLD was highly stable to heat in the presence of lecithin. Further, it was found that heating raised the acid value and peroxide value of PS, and thus the PS produced was subject to breakdown by heat. Thus, it was found that heating could not be an effective means for deactivating PLD.

Comparative Example 2

Evaluation for PLD Removal by Treatment with Protease—1

The proteases listed in Table 2 were added to the phospholipid fraction I at 20 U per 1 g lecithin and reacted for one hour at 60° C. while stirring, and then the residual PLD activity was measured as discussed above. The results are shown in Table 2.

TABLE 2

| Protease | Residual PLD Activity (U/g Lecithin) |
|---|---|
| — | 41.5 |
| Bioprase conc. | 37.5 |
| Denapsin 10P | 38.5 |
| Denazyme AP | 39.2 |

From Table 2 it was found that the activity of PLD was not substantially reduced by treating with protease in an organic solvent.

Comparative Example 3

Evaluation for PLD Removal by Treatment with Protease—2

It is conceivable that as the protease treatment was performed in an organic solvent for Comparative Example 2, hydrolysis of the PLD protein by protease did not proceed. Thus, a portion of the phospholipid fraction I was picked and the organic solvent was removed under reduced pressure, and then the residue was dispersed in water and again treated with protease (5 U protease added per 1 g lecithin, 60° C., one hour). The results are shown in Table 3. The activity of the protease used was measured as discussed above.

TABLE 3

| Protease | | | Residual PLD Activity (U/g Lecithin) |
|---|---|---|---|
| Type | Product Name (manufacturer) | Source | |
| End Type | Pancidase (Yakult Pharmaceutical Ind. Co., Ltd) | *Aspergillus niger* | 12.5 |
| | Protease YP-SS (Yakult Pharmaceutical Ind. Co., Ltd) | *Aspergillus niger* | 9.3 |
| | Protease P-3G (Amano Enzyme Inc.) | *Aspergillus mellens* | 10.8 |
| | Protease N (Amano Enzyme Inc.) | *Bacillus subtilis* | 13.6 |
| | Protease S (Amano Enzyme Inc.) | *Bacillus stearothermophilis* | 10.8 |
| | Protease F (Amano Enzyme Inc.) | *Rhizopus niveus* | 10.5 |
| | Bioprase conc. (Nagase ChemteX Corporation) | *Bacillus subtilis* | 12.8 |
| | Denapsin 10P (Nagase ChemteX Corporation) | *Aspergillus niger* | 12.1 |
| | XP415 (Nagase ChemteX Corporation) | *Rhizopus delemar* | 10.4 |
| End Type + Exo Type | Umamizyme (Amano Enzyme Inc.) | *Aspergillus oryzae* | 12.5 |
| | Protease M (Amano Enzyme Inc.) | *Aspergillus oryzae* | 15.2 |
| | Flavorzyme (Nagase ChemteX Corporation) | *Aspergillus oryzae* | 11.6 |
| | Denazyme AP (Nagase ChemteX Corporation) | *Aspergillus oryzae* | 11.3 |
| | Purified papain for food product (Nagase ChemteX Corporation) | papaya | 15.4 |
| | Peptidase R (Amano Enzyme Inc.) | *Rhizopus oryzae* | 16.3 |
| Umamizyme (2.5 U/g Lecithin) + Peptidase R (2.5 U/g Lecithin) | | — | 14.7 |
| No enzyme added | | — | 19.0 |
| No treatment | | — | 21.7 |

The PLD was deactivated only by approximately half even with the protease treatment under the conditions as mentioned here. It was found that an adequate effect could not be obtained on PLD deactivation.

Comparative Example 4

Evaluation for PLD Removal by Treatment with Acetone

Acetone was added to the phospholipid fraction I to denature and aggregate the PLD, then filtered, and then the residual PLD activity was measured. The results are shown in Table 4.

TABLE 4

| Treatment | | Residual PLD Activity (U/g Lecithin) |
|---|---|---|
| Solvent | Amount of Solvent Used | |
| Acetone | 4/10 (v/v) of phospholipid fraction I | 24.8 |
| Acetone | 5/10 (v/v) of phospholipid fraction I | 24.3 |
| Acetone | 6/10 (v/v) of phospholipid fraction I | 21.0 |
| | No treatment | 30.4 |

As seen from the results of Table 4, the activity of PLD was reduced only slightly after treatment with acetone. Increasing the amount of acetone added resulted in a decrease in the activity of PLD. However, lecithin was precipitated in an amount of acetone added more than 6/10 of the volume of the phospholipid fraction I, which was not preferable. In general, enzymes have a low tolerance to organic solvents such as acetone. However, it could be deduced from these results that the tolerance of PLD to the solvent would be increased in the presence of lecithin.

Comparative Example 5

Evaluation for PLD Removal by Washing with Aqueous NaCl Solution

The phospholipid fraction I was washed with an aqueous solution of NaCl, and then the residual PLD activity was measured. Table 5 shows the results, along with the concentrations and the amounts used of the aqueous solution of NaCl. The washing treatment includes adding an aqueous solution of NaCl to the phospholipid fraction I and thoroughly mixing by agitation, and then separating and removing the water phase by centrifugation or still standing. In the examination examples that follow, the washing treatment was carried out in the same manner.

TABLE 5

| Amount of Aqueous NaCl Solution Used | Residual PLD Activity (U/g Lecithin) NaCl Concentration | | |
|---|---|---|---|
| | 5% (w/v) | 15% (w/v) | 20% (w/v) |
| 1/10 (v/v) of phospholipid fraction I | 23.4 | 22.5 | 23.7 |
| 2/10 (v/v) of phospholipid fraction I | 23.4 | 21.3 | 21.6 |
| 3/10 (v/v) of phospholipid fraction I | 23.6 | 20.9 | 22.6 |
| No washing | | 40.6 | |

Next, the pH of the aqueous solution of 15 w/v % NaCl (hereinafter this may be referred to simply as "15% NaCl") was varied and the washing treatment was performed, and the residual PLD activity was measured. The amount used of 15% NaCl was 1/10 (v/v) of the amount of the phospholipid fraction I. The results are shown in Table 6.

TABLE 6

| Treatment | Residual PLD Activity (U/g Lecithin) |
|---|---|
| pH 2 | 16.5 |
| pH 3 | 16.7 |
| pH 4 | 17.5 |
| pH 5 | 15.9 |
| pH 6 | 14.9 |
| pH 7 | 14.5 |

TABLE 6-continued

| Treatment | Residual PLD Activity (U/g Lecithin) |
|---|---|
| pH 8 | 16.2 |
| pH 9 | 15.4 |
| No pH adjustment | 16.6 |
| No treatment | 37.6 |

Further, the number of washes with 15% NaCl was varied and the residual PLD was measured. The amount of 15% NaCl used was 1/10 (v/v) of the amount of the phospholipid fraction I. The results are shown in Table 7.

TABLE 7

| Number of Washes with 15% NaCl | Residual PLD Activity (U/g Lecithin) |
|---|---|
| 0 times | 58.4 |
| 1 time | 30.4 |
| 2 times | 24.1 |
| 3 times | 20.9 |

The results of Tables 5 to 7 indicate that the activity of PLD could be reduced by approximately half by washing with an aqueous NaCl solution. However, no remarkable effect was observed on PLD removal due to varying the pH or the number of the washing treatment.

Comparative Example 6

Evaluation of PLD Removal by Adsorbent

The phospholipid fraction I was treated with an adsorbent, and then the residual PLD activity was measured. The adsorbents listed in Table 8 were added 0.1 g per 1 ml phospholipid fraction I, and contacted for one hour at room temperature, and then the adsorbent was removed by filtration. For comparison, the washing treatment of the phospholipid fraction I was also performed using 15% (w/v) NaCl in an amount that is 1/10 (v/v) of the amount of the phospholipid fraction I. The results are shown in Table 8. In Table 8, "aqueous NaCl solution wash+magnesium sulfate" or "aqueous NaCl solution wash+activated clay" refers to that the phospholipid fraction I was washed with 15% NaCl in an amount that is 1/10 (v/v) of the amount of the phospholipid fraction I, and then treated with magnesium sulfate or activated clay to adsorption.

TABLE 8

| Treatment | Residual PLD Activity (U/g Lecithin) |
|---|---|
| No treatment | 14.2 |
| Aqueous NaCl Solution Wash (1 time) | 6.2 |
| Magnesium Sulfate | 9.8 |
| Activated Clay | 3.0 |
| Kaoline | 5.4 |
| Bentonite | 9.1 |
| Cellulose (Cell powder P100 made by Naigai seihun) | 6.7 |
| Aqueous NaCl Solution Wash + Magnesium Sulfate | 7.4 |
| Aqueous NaCl Solution Wash + Activated Clay | 4.9 |

It is apparent from the results in Table 8 that the treatment with an adsorbent resulted in a decrease in the activity of PLD which was not remarkable and which was comparable to that at washing with 15% NaCl. The activity of PLD was reduced to approximately 25% by the treatment with activated clay, which is conceivably is more effective than the NaCl wash. However, the treatment with activated clay in combination with the NaCl wash did not produce a further effect in removing PLD activity.

Comparative Example 7

Evaluation for PLD Removal by Washing with a Water-containing Organic Solvent

The phospholipid fraction I was washed using a solvent mixture of water with a polar organic solvent as listed in Table 9, and then the residual PLD activity was measured. The amount of solvent mixture used in the washing was 6/10 (v/v) of the amount of the phospholipid fraction I. For comparison, the washing treatment of the phospholipid fraction I was performed also using 15% (w/v) NaCl at 1/10 (v/v) of the amount of the phospholipid fraction I. The results are shown in Table 9.

TABLE 9

| Treatment | Residual PLD Activity (U/g Lecithin) |
| --- | --- |
| No treatment | 34.2 |
| 15% (w/v) NaCl wash | 13.6 |
| 67% (v/v) Isopropanol wash | 11.4 |
| 67% (v/v) Acetone wash | 8.6 |
| 67% (v/v) Ethanol wash | 8.4 |
| 67% (v/v) Methanol wash | 8.2 |

The washing treatments with 67% acetone, 67% isopropanol, 67% ethanol, and 67% methanol was more effective than the NaCl wash, but an adequate decrease in PLD activity was not observed.

As in the results of the Comparative Examples 1 to 7, it was extremely difficult to adequately deactivate PLD using conventional methods. The following examination examples illustrate a novel method for enzyme activity removal to solve this problem.

<Development of the Novel Method>

Examination Example 1

Washing Combination

The phospholipid fraction I was washed using the combinations of solvents listed in Table 10, and then the residual PLD activity was measured. The amount of solvent mixture used in the wash was 6/10 (v/v) of the amount of the phospholipid fraction I. The results are shown in Table 10.

TABLE 10

| Treatment | Residual PLD Activity (U/g lecithin) |
| --- | --- |
| no treatment | 34.2 |
| 15% (w/v) NaCl wash → 67% acetone wash | 13.6 |
| 15% (w/v) NaCl wash → 67% ethanol wash | 11.4 |
| 15% (w/v) NaCl wash → 50% acetone wash | 12.8 |
| 15% (w/v) NaCl wash → 50% ethanol wash | 13.2 |
| 50% acetone containing 7.5% NaCl wash | below detectable limit |
| 50% ethanol containing 7.5% NaCl wash | below detectable limit |
| 50% isopropanol containing 7.5% NaCl wash | below detectable limit |
| 50% methanol containing 7.5% NaCl wash | below detectable limit |
| 50% glycerol containing 7.5% NaCl wash | below detectable limit |

As seen from the results of Table 10, when washing with a solvent obtained by mixing a 15% NaCl and a polar solvent in equal amounts (50% of acetone, isopropanol, ethanol, methanol, or glycerol, which contains 7.5% NaCl), PLD was below the detectable limit. In contrast, when washing with NaCl followed by washing with an aqueous solution of acetone or ethanol, the activity of PLD was reduced only to 33%-40%. In view of above, it was found that washing with a solvent mixture of water and an organic solvent, wherein the solvent mixture contains an inorganic metal salt, was effective for removing PLD. The detectable limit of PLD was 0.01 U per 1 g lecithin.

Examination Example 2

Evaluation for PLD Removal Using a Metal Salt Other than NaCl

The phospholipid fraction I was washed using 50% acetone containing a metal salt other than NaCl, and then the residual PLD activity was measured. The amount of solvent used in the washing was 6/10 (v/v) of the amount of the phospholipid fraction I. The results are shown in Table 11.

TABLE 11

| Treatment | Residual PLD Activity (U/g Lecithin) |
| --- | --- |
| No treatment | 24.2 |
| 50% acetone containing 7.5% NaCl wash | below detectable limit |
| 50% acetone containing 7.5% $Na_2SO_4$ wash | below detectable limit |
| 50% acetone containing 7.5% KCl wash | below detectable limit |
| 50% acetone containing 7.5% $CaCl_2$ wash | below detectable limit |
| 50% acetone containing 7.5% $MgSO_4$ wash | below detectable limit |

The results in Table 11 demonstrate that PLD can be removed using $Na_2SO_4$, KCl, $CaCl_2$, or $MgSO_4$ in place of NaCl, as well as using NaCl, as the inorganic metal salt.

Examination Example 3

Optimization of Washing with a Water-Containing Polar Solvent that Contains an Inorganic Metal Salt Based on the results of the examination examples as discussed above, the optimal conditions were examined for the polar solvent concentration, the inorganic metal salt concentration, and the amount used with respect to the phospholipid fraction I. In this examination, acetone was used as the polar solvent and NaCl was used as the inorganic metal salt. The results are shown in Table 12.

TABLE 12

| Treatment | | Residual PLD Activity |
| --- | --- | --- |
| Wash Solvent | Amount Use*[1] | (U/g Lecithin) |
| 50% acetone containing 7.5% NaCl | 6/10 | below detectable limit |
| | 5/10 | 0.08 |
| | 4/10 | 0.13 |
| | 3/10 | 0.30 |
| | 2/10 | 0.92 |
| | 1/10 | 8.91 |
| 50% acetone | 6/10 | 9.89 |
| 50% acetone containing 5.0% NaCl | 6/10 | 0.40 |
| 50% acetone containing 2.5% | 6/10 | 10.68 |

TABLE 12-continued

| Treatment | | Residual PLD Activity |
|---|---|---|
| Wash Solvent | Amount Use*1 | (U/g Lecithin) |
| NaCl | | |
| 25% acetone containing 7.5% NaCl | 6/10 | 6.51 |
| No treatment | | 18.75 |

*1 the amount of wash solvent/phospholipid fraction I (v/v)

The results of Table 12 show that the residual PLD activity was reduced as the amount of solvent mixture used in the wash was increased. When washing was performed with a solvent mixture in an amount of 6/10 (v/v) of the volume of the phospholipid fraction I, the residual enzyme was more efficiently removed with an increase in the NaCl concentration, and when the salt concentrations were same, the residual enzyme was more efficiently removed with an increase in the acetone concentration.

Examination Example 4

Evaluation for the Residual Protein

The washing of the phospholipid fraction I with a solvent mixture of 50% acetone containing 7.5% NaCl at 6/10 (v/v) of the volume of the phospholipid fraction I was repeated one to three times, and then the level of the residual protein in the phospholipid fraction I was measured. The quantification of the protein was performed as discussed above. The results are shown in Table 13.

TABLE 13

| | Residual Protein (µg/g Lecithin) | Residual PLD Activity (U/g Lecithin) |
|---|---|---|
| Raw Lecithin (before reaction) | 23 | below detectable limit |
| Before wash | 100.1 | 18.75 |
| After first wash | 45.3 | below detectable limit |
| After second wash | 20 | below detectable limit |
| After third wash | below detectable limit | below detectable limit |

As shown in Table 13, it could be confirmed that the protein was reduced to below the detectable limit by repeating the process of washing with a water-containing organic solvent that contains an inorganic metal salt one to three times. This indicates that not only the denaturation of phospholipids by residual enzyme is prevented, but also the risk of inducing an allergy can be effectively reduced.

As shown in the results of Examination Examples 1 to 4, a newly developed method of washing with a water-containing polar solvent that contains an inorganic metal salt could efficiently remove residual PLD activity and reduce the protein to below the detectable limit. Therefore, it could be confirmed that this method could be an effective means for eliminating residual PLD activity and for purification.

<Application to a Hydrolysis Reaction and to Other Enzymes>

Examination Example 5

Evaluating for the Removal of Residual Enzyme Activity from a Hydrolysis Reaction Enzyme Solution Both the phospholipid fraction II and the phospholipid fraction III contain the product PA and the enzyme PLD. The phospholipid fraction IV contains the product LPA and the enzymes PLD and $PLA_2$. The phospholipid fraction V contains the product LPA and the enzymes PLD and lipase. The phospholipid fraction VI contains the product PA and PLD and protease. Accordingly, a method of purifying the product from the hydrolysate of the phospholipids, that is, a method of removing the enzyme remaining in the product, was examined. The phospholipid fraction I obtained by the base exchange reaction was also used for comparison.

In the phospholipid fractions I and III to V, the washing treatment was performed as in Examination Example 3 with proviso that adding 50% acetone containing 15 w/v % NaCl at 6/10 (V/V). Since the phospholipid fractions II and VI are water-based solvents containing PA, the washing treatment was performed as in Examination Example 3 with proviso that separately adding NaCl at 7.5% (w/v) and acetone at twice the volume (v/v) and heptane at an equal volume (v/v) to the volume of the phospholipid fraction and agitating them, so that extraction of PA and washing could be simultaneously achieved. The residual activity of each of PLD, $PLA_2$, lipase, and protease was measured as discussed above. The results are shown in Table 14.

TABLE 14

| | Residual Enzyme Activity (U/g Lecithin) | | | |
|---|---|---|---|---|
| Specimen | PLD | $PLA_2$ | Lipase | Protease |
| Phospholipid Fraction I | below detectable limit | — | — | — |
| Phospholipid Fraction II | below detectable limit | — | — | — |
| Phospholipid Fraction III | below detectable limit | — | — | — |
| Phospholipid Fraction IV | below detectable limit | below detectable limit | — | — |
| Phospholipid Fraction V | below detectable limit | — | below detectable limit | — |
| Phospholipid Fraction VI | below detectable limit | — | — | below detectable limit |

The results of Table 14 show that all of the enzymes were below the detectable limit after washing with an aqueous acetone solution containing NaCl in all of the reaction types (base exchange reaction or hydrolysis) and in all of the reaction systems (reactions using organic solvent or water-based reactions). The detectable limit of the enzymes used was 0.01 U of PLD, 20.1 U of $PLA_2$, 1 U of lipase, and 1 U of protease, per 1 g lecithin, respectively. From this it was found that the method of the present invention could be used, for removal of the residual activity of the enzyme from the liquid enzyme reaction mixture obtained by hydrolysis of the phospholipid, or for an liquid enzyme reaction mixture to which a protease has been added to deactivate the enzyme, as well as for a base exchange liquid enzyme reaction mixture. In particular, the fact that PLD was below the detectable limit in phospholipid fractions II and VI demonstrates that extraction from a water-based solvent and washing can be concurrently achieved, and further demonstrates that it is effective to separately add the components of the solvent mixture for washing and then blend them. This indicates that an organic solvent, water, or an inorganic metal salt which has already been included in the liquid enzyme reaction mixture, wherein the organic solvent, water, or inorganic metal salt can constitute the solvent mixture for washing, can be regarded as the components of the wash solvent, and thus it is possible to remove the activities of enzymes, such as PLD, which are used for the base exchange or hydrolysis of phospholipids, or enzymes which are used for deactivating those enzymes, by performing the washing treatment as in Examination Example 3 with the condition that supplementing with organic solvent, water, and inorganic metal salt to the levels as needed to reach the required amount and agitating them.

The results as discussed above indicate that the method of the present invention can be employed irrespective of the enzyme types. Further, it was found that the method of the present invention can be applied for both a base exchange reaction and a hydrolysis reaction, and can be applied regardless of whether the reaction system is a system which includes an organic solvent or a system which does not includes an organic solvent (i.e., is water-based). Because the method of the present invention makes it possible to remove impurities such as proteins, including enzymes, from various types of reaction systems as discussed above, the method of the present invention is conceivably a highly generalized method that can serve as a method for removing enzyme and a method for purifying phospholipids.

According to the present invention, it is possible to easily remove the enzyme and protein included in the liquid enzyme reaction mixture and the reaction product on the base exchange reaction or hydrolysis reaction of phospholipid by using the enzyme, without a treatment such as heating. Thus, it becomes possible to easily produce various phospholipids that have a reduced risk of inducing an allergy, that retain a high quality and that have excellent storage stability. These high quality phospholipids can be used in various industrial fields, including but not limited to food applications.

The invention claimed is:

1. A method of removing an enzyme from a liquid enzyme reaction mixture, comprising:
    a. providing the liquid enzyme reaction mixture, wherein the liquid enzyme reaction mixture is produced by:
        i. a phospholipid base exchange reaction comprising reacting, in the presence of an enzyme, a phospholipid with a compound having an alcoholic hydroxyl group, wherein the enzyme is capable of transferring a phosphatidyl group of the phospholipid to the compound, and wherein the compound having an alcoholic hydroxyl group is selected from the group consisting of an alcohol, a saccharide, and a cyclic compound having a hydroxyl group; or
        ii. a phospholipid hydrolysis reaction comprising enzymatically hydrolyzing a phospholipid in the presence of water; and
        optionally adding a protease to the phospholipid base exchange reaction (i) or the phospholipid hydrolysis reaction (ii) to deactivate the enzyme;
    b. adding to the liquid enzyme reaction mixture an organic solvent; at least one inorganic metal salt selected from the group consisting of sodium salt, potassium salt, calcium salt, magnesium salt, and ammonium salt; and optionally water, to remove the enzyme and/or the protease and to wash the liquid enzyme reaction mixture, thereby removing the enzyme from the liquid enzyme reaction mixture;
    wherein the enzyme is selected from the group consisting of lipase, phospholipase $A_2$ ($PLA_2$), and phospholipase D (PLD).

2. The method of claim 1, wherein the organic solvent is a polar organic solvent.

3. The method of claim 2, wherein the polar organic solvent is at least one solvent selected from the group consisting of acetone, ethanol, methanol, isopropanol, and glycerol.

4. The method of claim 1, wherein in step (b) the adding comprises adding a solvent mixture comprising an organic solvent, an inorganic metal salt, and water to wash the liquid enzyme reaction mixture.

5. The method according to claim 4, wherein the solvent mixture comprises:
    a. water in an amount of 30 to 70% (v/v);
    b. the organic solvent in an amount of 30 to 70% (v/v); and
    c. the inorganic metal salt in an amount of 3 to 25% (w/v).

* * * * *

UNITED STATES PATENT AND TRADEMARK OFFICE
CERTIFICATE OF CORRECTION

PATENT NO. : 7,709,238 B2
APPLICATION NO. : 10/592858
DATED : May 4, 2010
INVENTOR(S) : Liu et al.

Page 1 of 1

It is certified that error appears in the above-identified patent and that said Letters Patent is hereby corrected as shown below:

On the Title Page: Item (54) Title, Lines 1-4, "METHOD FOR REMOVING ENZYME AND METHOD OF BASE EXCHANGE OR HYDROLYSIS OF PHOSPHOLIPID USING THE SAME"
should read
-- METHOD OF REMOVING ENZYME AND METHOD OF BASE EXCHANGE OR HYDROLYSIS OF PHOSPHOLIPID USING THE SAME --

Signed and Sealed this

Twenty-fourth Day of August, 2010

David J. Kappos
*Director of the United States Patent and Trademark Office*

UNITED STATES PATENT AND TRADEMARK OFFICE
CERTIFICATE OF CORRECTION

PATENT NO. : 7,709,238 B2 Page 1 of 1
APPLICATION NO. : 10/592858
DATED : May 4, 2010
INVENTOR(S) : Liu et al.

It is certified that error appears in the above-identified patent and that said Letters Patent is hereby corrected as shown below:

On the Title Page: Item (54) and at Column 1, lines 1-4, Title "METHOD FOR REMOVING ENZYME AND METHOD OF BASE EXCHANGE OR HYDROLYSIS OF PHOSPHOLIPID USING THE SAME"
should read
-- METHOD OF REMOVING ENZYME AND METHOD OF BASE EXCHANGE OR HYDROLYSIS OF PHOSPHOLIPID USING THE SAME --

This certificate supersedes the Certificate of Correction issued August 24, 2010.

Signed and Sealed this

Twenty-eighth Day of September, 2010

David J. Kappos
*Director of the United States Patent and Trademark Office*